United States Patent
Shen et al.

(10) Patent No.: US 11,596,450 B2
(45) Date of Patent: Mar. 7, 2023

(54) LOW-PROFILE OFFSET-TYPE SPINAL FUSION DEVICE

(71) Applicant: Industrial Technology Research Institute, Hsinchu (TW)

(72) Inventors: Hsin-Hsin Shen, Taipei (TW); Pei-I Tsai, Hsinchu (TW); Chih-Chieh Huang, Miaoli County (TW); Kuo-Yi Yang, Hsinchu (TW); Yi-Hung Wen, Hsinchu (TW); Wei-Lun Fan, Miaoli County (TW); Fang-Jie Jang, Keelung (TW); Shih-Ping Lin, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/462,722

(22) Filed: Aug. 31, 2021

(65) Prior Publication Data

US 2022/0175423 A1    Jun. 9, 2022

Related U.S. Application Data

(60) Provisional application No. 63/122,096, filed on Dec. 7, 2020.

(30) Foreign Application Priority Data

Jan. 29, 2021 (TW) ................................ 110103414

(51) Int. Cl.
    *A61B 17/70* (2006.01)
(52) U.S. Cl.
    CPC ...... *A61B 17/7041* (2013.01); *A61B 17/7002* (2013.01); *A61B 17/7032* (2013.01)

(58) Field of Classification Search
    CPC .......... A61B 17/7041; A61B 2090/037; A61B 17/7034; A61B 17/7049; A61B 17/7032;
    (Continued)

(56) References Cited

U.S. PATENT DOCUMENTS 5,487,744 A * 1/1996 Howland ........... A61B 17/7041
                                                         606/264
5,776,134 A    7/1998 Howland
(Continued)

FOREIGN PATENT DOCUMENTS

CN       108498152 A    9/2018
CN       110290756 A    9/2019
(Continued)

OTHER PUBLICATIONS

Iyer et al., "A Modified Technique forOccipitocervical Fusion UsingCompressed Iliac Crest AllograftResults in a High Rate of Fusion in thePediatric Population", Jul. 17, 2017, World Neurosurgery.

(Continued)

*Primary Examiner* — Jan Christopher L Merene
*Assistant Examiner* — Anna V. Little
(74) *Attorney, Agent, or Firm* — WPAT, PC

(57) ABSTRACT

A low-profile offset-type spinal fusion device includes a first screw, a connection base, a nut and a compression part. The first screw has an external thread and a flange. The connection base includes a penetration part and a connection part disposed no higher than the penetration part, and can sleeve the first screw through a first hole of the penetration part to contact the flange with opposite ends of the first screw protruding out of the first hole. The nut, used to engage the first screw, has a bottom surface to contact against the penetration part. When the first screw is installed by penetrating the first hole, the nut and the flange are located to (Continued)

opposite ends of the first hole. The compression part is to screw into a cavity of the connection part for depressing a connecting bar tightly in the cavity.

12 Claims, 11 Drawing Sheets

(58) Field of Classification Search
CPC .............. A61B 17/705; A61B 17/7052; A61B 17/8042; A61B 17/8047
See application file for complete search history.

(56) References Cited

U.S. PATENT DOCUMENTS

| | | | |
|---|---|---|---|
| 6,328,739 B1 * | 12/2001 | Liu ................... | A61B 17/7041 606/264 |
| 6,709,434 B1 * | 3/2004 | Gournay ............ | A61B 17/7037 606/272 |
| 7,670,360 B2 | 3/2010 | Catbagan et al. | |
| 9,956,010 B2 | 5/2018 | Richelsoph et al. | |
| 2003/0163133 A1 * | 8/2003 | Altarac .............. | A61B 17/7035 606/264 |
| 2005/0010216 A1 * | 1/2005 | Gradel ............... | A61B 17/7041 606/264 |
| 2006/0039772 A1 * | 2/2006 | Matthys-Mark ........ | F16B 35/06 411/5 |
| 2006/0217715 A1 | 9/2006 | Serhan et al. | |
| 2007/0100339 A1 * | 5/2007 | Clement ............ | A61B 17/7037 606/86 A |
| 2011/0196424 A1 * | 8/2011 | Bishop ............... | A61B 17/7037 606/279 |
| 2011/0245873 A1 * | 10/2011 | Winslow ............ | A61B 17/7031 606/264 |
| 2012/0143256 A1 | 6/2012 | Winslow et al. | |
| 2014/0012333 A1 * | 1/2014 | Tornier .............. | A61B 17/8605 606/308 |
| 2017/0172631 A1 * | 6/2017 | Mosnier ............. | A61B 17/7043 |
| 2017/0333084 A1 * | 11/2017 | Blakemore .......... | A61B 17/809 |
| 2020/0069346 A1 * | 3/2020 | Wolfe ................ | A61B 17/7082 |

FOREIGN PATENT DOCUMENTS

| | | |
|---|---|---|
| CN | 110769770 A | 2/2020 |
| CN | 111200981 A | 5/2020 |
| TW | 237648 U | 1/1995 |
| TW | 268278 U | 1/1996 |
| TW | 382993 U | 2/2000 |
| TW | I243047 | 11/2005 |
| TW | 200724071 A | 7/2007 |
| TW | 200934441 A | 8/2009 |
| TW | M409817 | 8/2011 |
| TW | M425654 | 4/2012 |
| TW | 201811260 A | 4/2018 |

OTHER PUBLICATIONS

Chechik et al. "A new pelvic rod system for the surgicalcorrection and fixation of pelvicobliquity in pediatric neuromuscularscoliosis", Feb. 2011, Journal of Children's Orthopaedics.
Gaines, "The use of pedicle-screw internal fixationfor the operative treatment of spinaldisorders", Oct. 2000, Journal of Bone and Joint Surgery.
Hicks et al. "Complications of Pedicle Screw Fixationin Scoliosis SurgeryA Systematic Review", 2010, Lippinocott Williams & Walkins.
PEng et al. "Biomechanical Comparison of 2 DifferentPedicle Screw SystemsDuring the Surgical Correction of AdultSpinal Deformities", Mar. 17, 2014, Scoliosis Research Society.
Wang et al. "Pediatric Lumbar Pedicle ScrewPlacement Using Navigation TemplatesA Cadaveric Study", 2017, Indian Journal of Orthopaedics Pubished by Wolters Kluwer-Medknow.
Kuh et al. "A Novel Blasted and Grooved LowProfile Pedicle Screw Able toResist High Compression Bending Loads" May 4, 2012, The Korean Spinal Neurosurgery Society.
Liu et al. "Biomechanical comparison of pediclescrewfixation strength in synthetic bones:Effects ofscrew shape, core/thread profile andcementaugmentation", Feb. 21, 2020, PLOS One.
Wojewnik et al. "Biomechanical evaluation of a lowprofile, anchored cervicalinterbody spacer device in the setting ofprogressiveflexion-distraction injury of the cervicalspine", Feb. 22, 2012, Springer-Verlag.
Schroerlucke et al. "How Does a Novel Monoplanar PedicleScrew Biomechanically Relative toMonoaxial and Polyaxial DesignsPerform", Aug. 12, 2013, Clinical Orthopaedics and Related Research.
Taiwan Patent Office "TW Notice of Allowance" dated Jul. 9, 2021, Taiwan.

* cited by examiner

LOW-PROFILE OFFSET-TYPE SPINAL FUSION DEVICE

CROSS REFERENCE TO RELATED APPLICATION

This application claims the benefits of U.S. provisional application Ser. No. 63/122,096, filed on Dec. 7, 2020, and Taiwan application Serial No. 110103414, filed on Jan. 29, 2021, the disclosures of which are incorporated by references herein in its entirety.

TECHNICAL FIELD

The present disclosure relates in general to a medical technology, and more particularly to a low-profile offset-type spinal fusion device.

BACKGROUND

In the art, a pedicle screw for spine fusion usually has a multi-piece head so as to make multi-axis applications possible. However, due to assembly tolerances, the multi-piece head usually has an irreducible size. Therefore, the length of the current pedicle screw already in the marketplace is never shorter than 15 mm.

Generally speaking, the distance from the spinous process to the epidermis of a normal adult is about 32-50 mm. Then, after a pedicle screw is implanted, the distance from a top end of the pedicle screw to the epidermis is about 10-20 mm. As for infants and spine deformities, their subcutaneous thickness is usually less than 20 mm, and thus, in the area where the spinal curvature changes, the upper edges of two adjacent pedicle screws would be likely to interfere with each other.

Since over protruding pedicle screws are not easily adopted to those who provide only limited back space or to the soft tissues that are easy to cause friction on the skin and muscles, thus the application of the pedicle screw would cause serious discomfort. In other words, for normal adults, infants, people with insufficient distance between spine and epidermis, deformity of the back, and patients whose upper bodies need long-time rest, the aforesaid pedicle screw for the spinal fusion device is definitely not a good choice.

Accordingly, a topic how to develop a "low-profile offset-type spinal fusion device" having single-axial screws with less length, no discomfort and no inter-screw interference is definitely urgent to be solved to the skill in the art.

SUMMARY

In one embodiment of this disclosure, a low-profile offset-type spinal fusion device includes a first screw, a connection base, a nut and a compression part. The first screw is furnished with an external thread and an annular flange. The connection base includes a penetration part and a connection part. The penetration part is furnished with a first hole. The connection part, disposed at a side of the penetration part, has a top surface thereof located at the same level as or lower than a top surface of the penetration part, and a cavity for allowing a connecting bar to penetrate therethrough. The connection base utilizes the first hole to sleeve outside the first screw so as to have the first hole to contact against a top portion of the flange, and to have opposite ends of the first screw to protrude out of the first hole. The nut, used to engage the first screw, has a bottom surface thereof to contact against the penetration part. When the first screw is installed by penetrating the first hole, the nut and the flange are located to opposite ends of the first hole. The compression part is used to be screwed into the cavity so as to depress the connecting bar tightly in the cavity.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
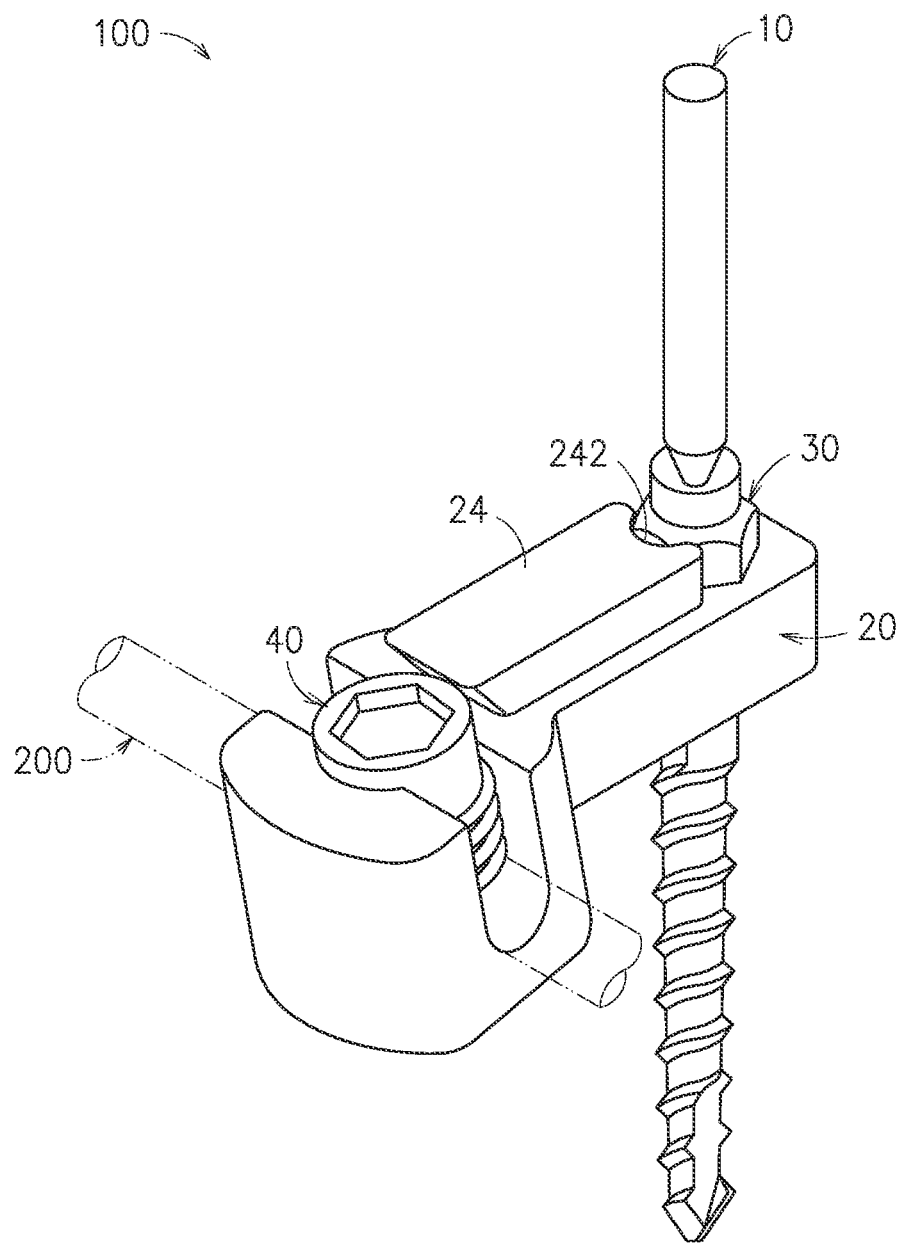
FIG. 1 is a schematic perspective view of an embodiment of the low-profile offset-type spinal fusion device in accordance with this disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
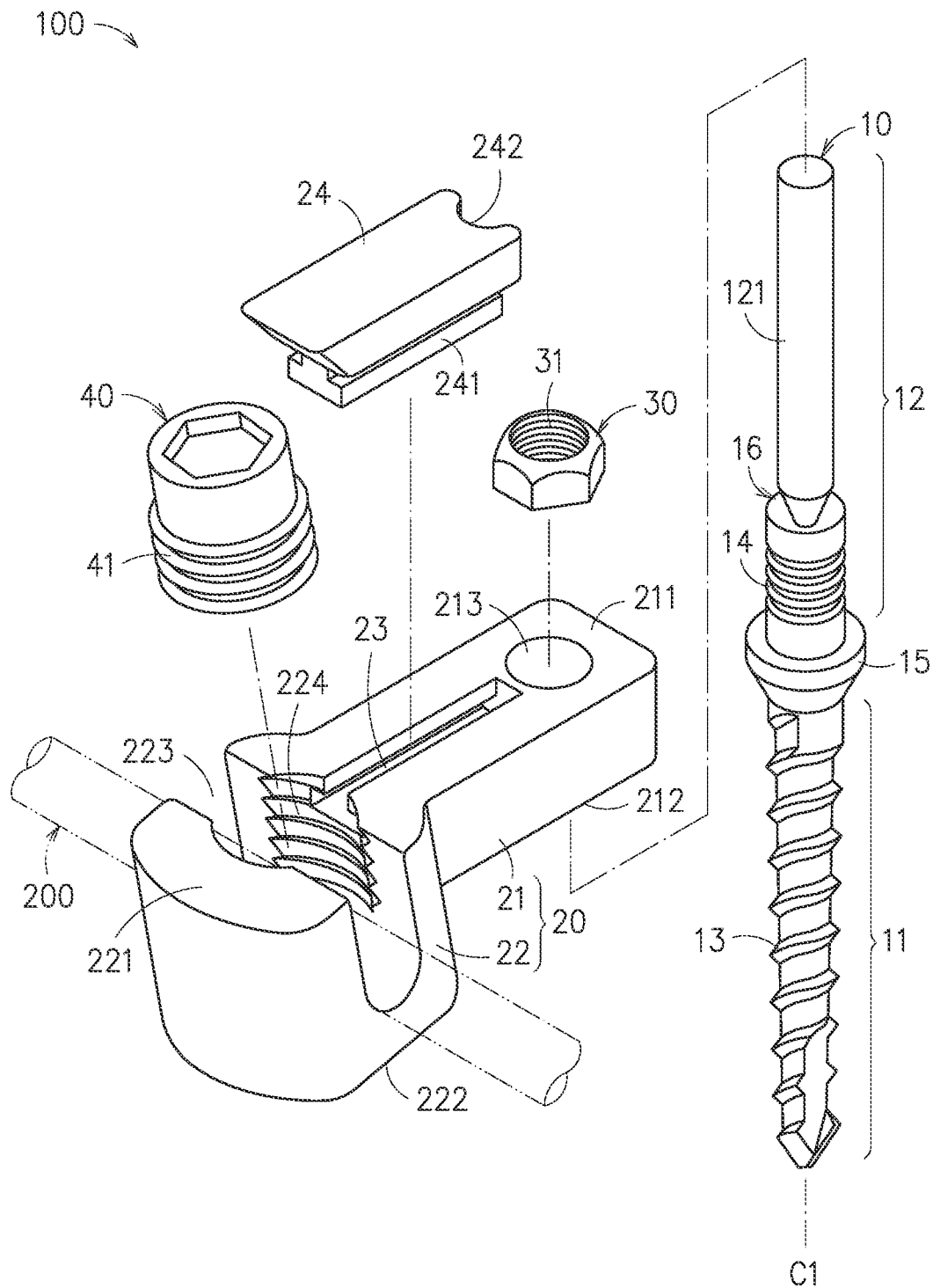
FIG. 2 is a schematic exploded view of FIG. 1.

Referring to FIG. 1 and FIG. 2, in this embodiment of the present disclosure, the low-profile offset-type spinal fusion device 100 includes a first screw 10, a connection base 20, a nut 30 and a compression part 40, in which the connection base 20 allows a connecting bar 200 to penetrate therethrough.

Figure 3:
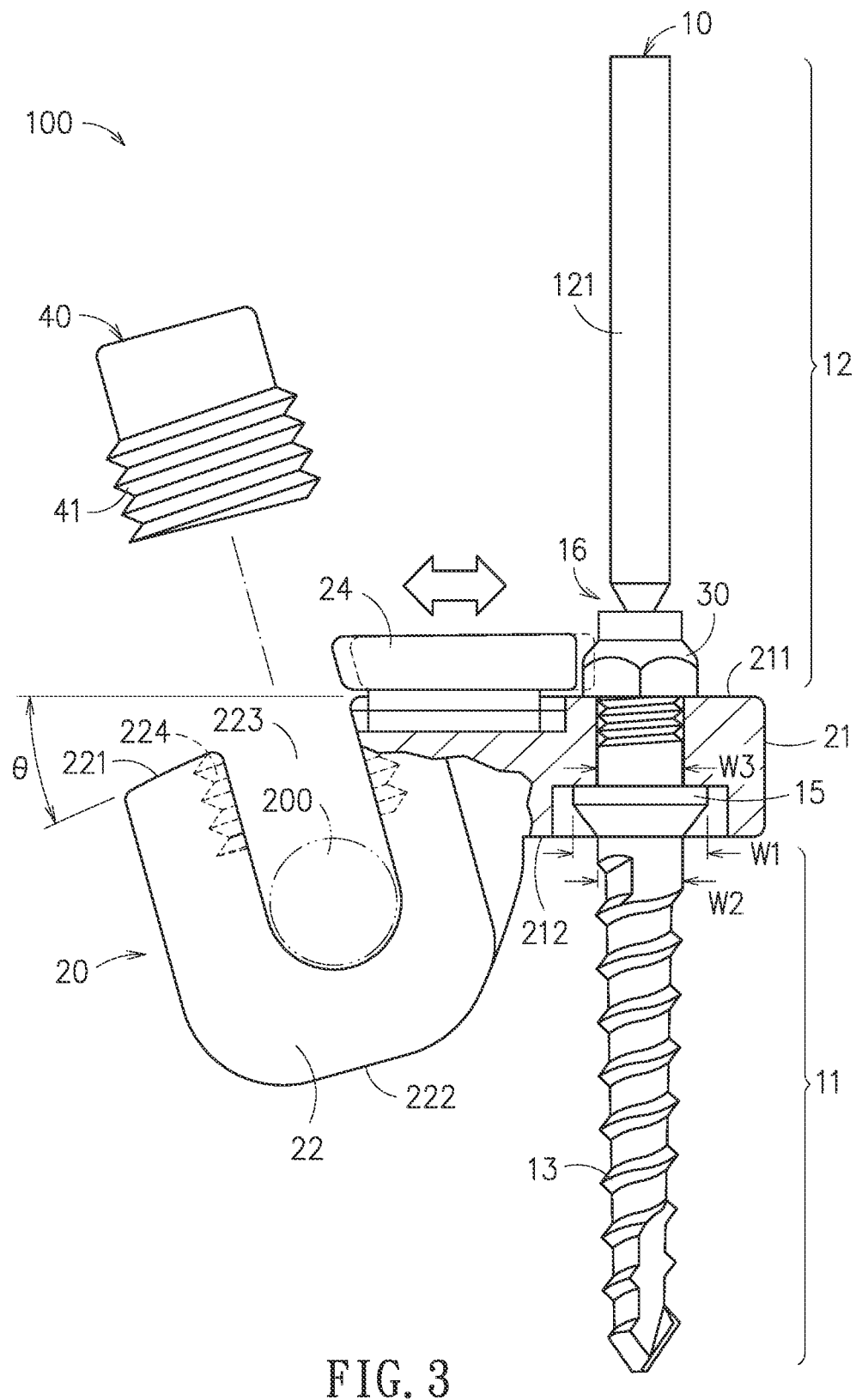
FIG. 3 is a schematic partly cross-sectional view of the embodiment of FIG. 1.

Referring to FIG. 2 and FIG. 3, the first screw 10, defined with an axial direction C1, has a first section 11 and a second section 12 connected linearly with the first section 11. The first section 11 is furnished with a first external thread 13, and the second section 12 is furnished with a second external thread 14. In this disclosure, the first external thread 13 and the second external thread 14 may have the same or different specifications. In this embodiment, the first external thread 13 and the second external thread 14 have different specifications. The first external thread 13 has a larger tooth with a wider pitch, while the second external thread 14 has a finer tooth with a shorter pitch.

The first screw 10 is furnished with an annular flange 15 located roughly at a middle portion thereof. In this embodiment, the flange 15 is disposed between the first section 11 and the second section 12. In detail, the first section 11 and the second section 12 are located to two opposite sides of the flange 15. An outer diameter W1 of the flange 15 is larger than the outer diameters W2 and W3 of the first section 11 and the second section 12, respectively.

Figure 4:
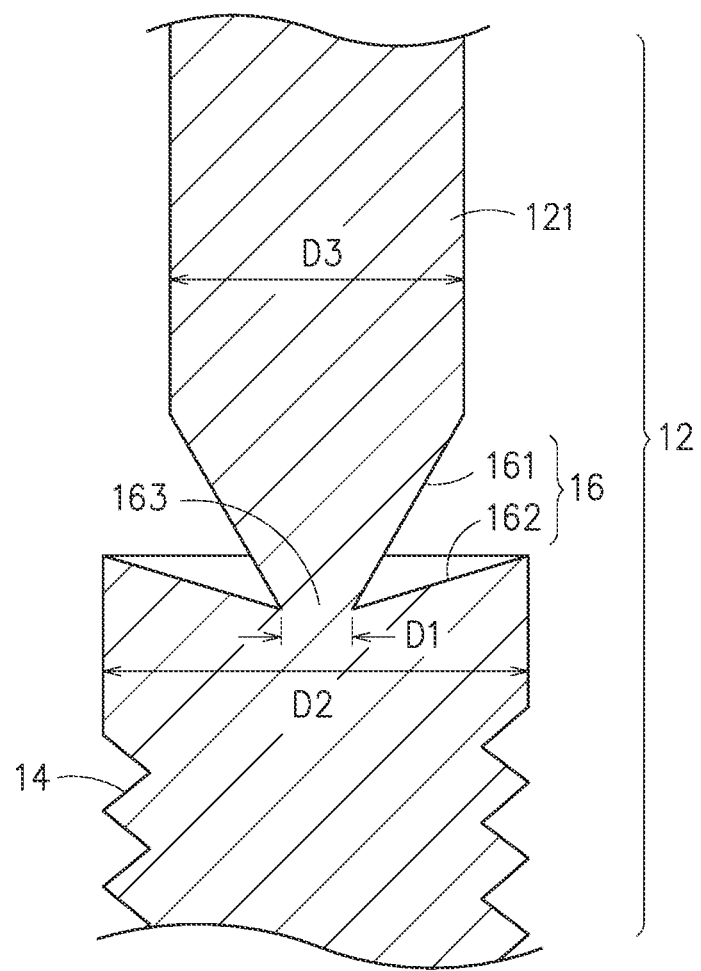
FIG. 4 demonstrates schematically the tapered neck area of the embodiment of FIG. 1 in a cross-sectional view.

Referring to FIG. 3 and FIG. 4, the second section 12 is structured to have a tapered neck area 16. The tapered neck area 16 includes an inverted taper portion 161 and a concave portion 162. The inverted taper portion 161 is extended axially and shrunk gradually from the second section 12 toward the first section 11. The concave portion 162 is concaved from the second section 12 toward the first section 11. In addition, in this disclosure, the taper of the inverted taper portion 161 and the cavity of the concave portion 162 are not limited to any specific size.

Preferably, the concave portion 162 and the inverted taper portion 161 are concentric and connected at a central breakable interface 163. The central breakable interface 163 has a first diameter D1, the second section 12 has a second diameter D2, and the first diameter D1 is smaller than the second diameter D2. More practically, the first diameter D1 is less than or equal to 1.5 mm. The second section 12 is structured to form a removable part 121 extended from the tapered neck area 16. In this embodiment, the removable part 121 has a third diameter D3 less than the second diameter D2. However, in this disclosure, per practical requirements, the third diameter D3 can be larger than, less than, or equal to the second diameter D2.

Referring back to FIG. 2 and FIG. 3, the connection base 20 includes a penetration part 21 and a connection part 22.

The penetration part 21 has oppositely a first surface 211 and a second surface 212, in which the first surface 211 is a top surface of the penetration part 21, while the second surface 212 is a bottom surface thereof. In addition, the penetration part 21 is furnished with a first hole 213 to penetrate through from the first surface 211 to the second surface 212.

The connection part 22, disposed at one side of the penetration part 21, has oppositely a third surface 221 and a fourth surface 222. The third surface 221 is a top surface of the connection part 22, and the fourth surface 222 is a bottom surface thereof. In addition, the third surface 221 of the connection part 22 is furnished with a cavity 223 for allowing the connecting bar 200 to penetrate therethrough, and the cavity 223 is furnished with an internal thread 224.

The nut 30 is furnished with an internal thread 31 to match the second external thread 14 of the first screw 10, and the nut 30 is to sit right on the first surface 211 of the penetration part 21 by having the nut 30 and the flange 15 to dispose at opposite surfaces of the first hole 213. Thereupon, the first screw 10 can be screwed fixedly to the penetration part 21. In detail, the first hole 213 is configured to have different diameters in the penetration part 21. As shown in FIG. 3, the first hole 213 is a step hole having two diameters. The inner diameter of the first hole 213 close to the first surface 211 is about equal to or slightly greater than the outer diameter W3 of the second section 12, and the inner diameter of the first hole 213 close to the second surface 212 is about equal to or slightly greater than the outer diameter W1 of the flange 15. By having the second section 12 of the first screw 10 to penetrate upward (as shown in FIG. 3) through the first hole 213, then having a top surface of the flange 15 to contact against the inner shoulder portion inside the first hole 213 (formed due to the step hole configuration thereof), and finally having the nut 30 to engage the second external thread 14 of the first screw 10, the connection base 20 including the penetration part 21 can be fixed with the first screw 10 via the nut 30 and the flange 15 to tightly clamp the penetration part 21 in between. In another embodiment, the first hole 213 can be configured to be a through hole with a constant diameter, and the constant inner diameter of the first hole 213 is about equal to or slightly greater than the outer diameter W3 of the second section 12. In addition, at this embodiment, the flange 15 with an even larger outer diameter W1 would be stopped by the second surface 212 of the connection base 20, and thus the nut 30 can be applied to screw the first screw 10 to lock up the penetration part 21.

The compression part 40 has an external thread 41 to engage the internal thread 224 of the cavity 223. With the compression part 40 to screw into the cavity 223, the connecting bar 200 can be depressed tightly in the cavity 223.

As shown in FIG. 3, in this embodiment, the third surface 221 of the connection part 22 is not parallel to the first surface 211 of the penetration part 21. In detail, an angle θ ranging between 0° to 150° is formed between the third surface 221 and the first surface 211. With the slope formed by the angle θ, the third surface 221 is disposed lower than the first surface 211.

Figure 5A:
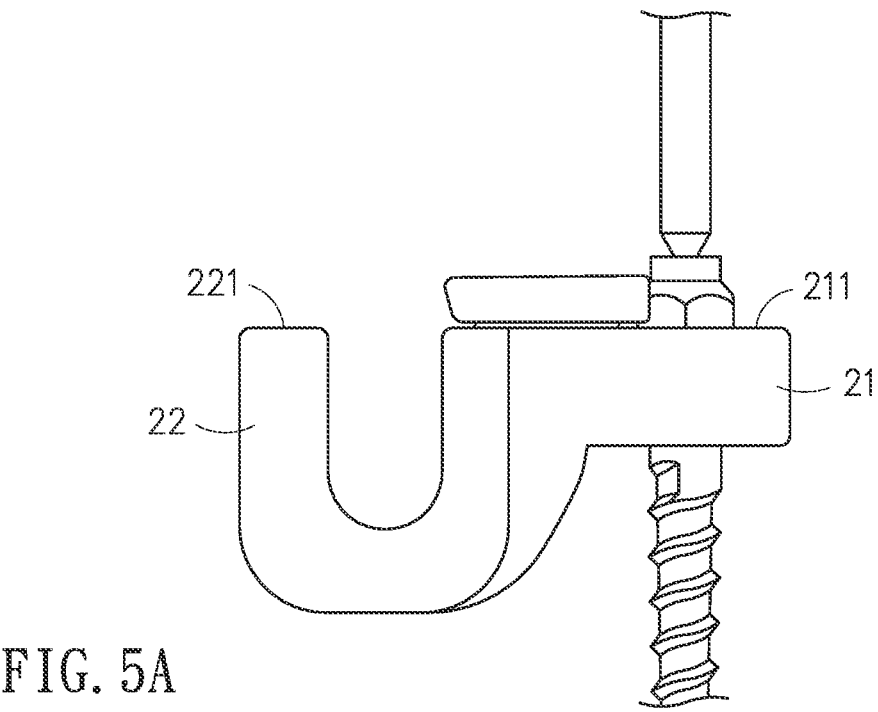
FIG. 5A and FIG. 5B demonstrate schematically two exemplary examples of the connection base for the low-profile offset-type spinal fusion device in accordance with this disclosure.
Figure 5B:
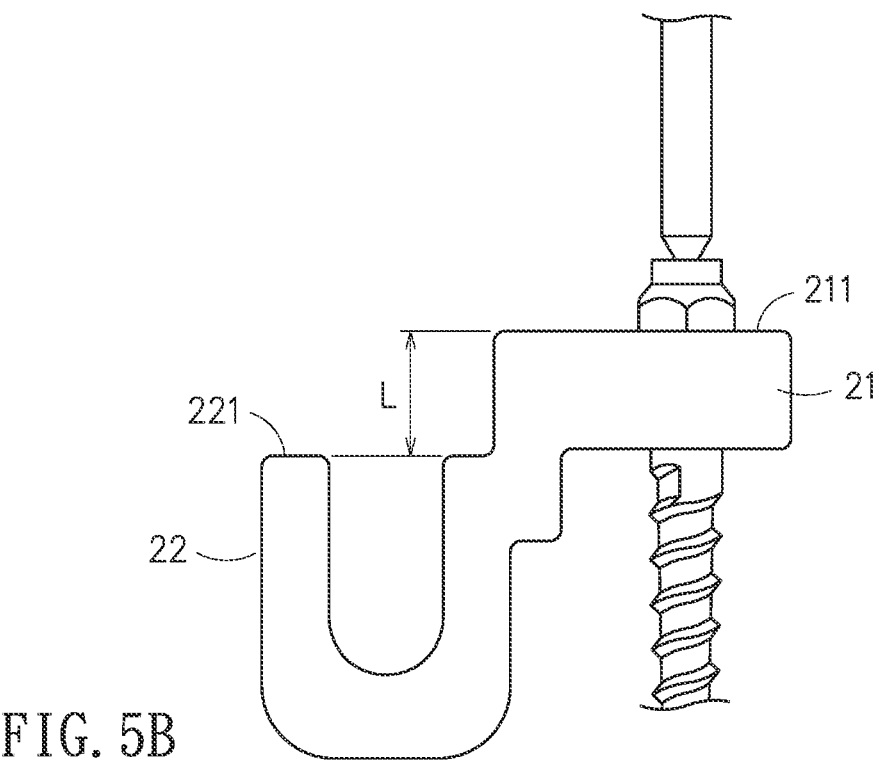

Beside the structure shown in FIG. 3, FIG. 5A and FIG. 5B show different structures for the connection base 20 thereof.

Referring to FIG. 5A, the third surface 221 and the first surface 211 are parallel to each other, and the third surface 221 is disposed at the same height with the first surface 211. Namely, the third surface 221 and the first surface 211 are coplanar. In other words, the angle θ between the third surface 221 and the first surface 211 is zero.

Referring to FIG. 5B, the third surface 221 is parallel to the first surface 211. However, the third surface 221 and the first surface 211 are not coplanar. Namely, as shown, the third surface 221 is lower than the first surface 211 with a distance L. In this disclosure, the distance L can be, but not limited to, less than or equal to 40 mm.

From aforesaid embodiments of FIG. 3, FIG. 5A and FIG. 5B, it can be understood that the connection base 20 of this disclosure may have different aspects. However, the only requirement for the penetration part 21 and the connection part 22 according to this disclosure is that the third surface 221 (i.e., the top surface of the connection part 22) is at the same level as or lower than the first surface 211 (i.e., the top surface of the penetration part 21).

Referring to FIG. 1 through FIG. 3, the connection base 20 is furnished with a slippery groove 23 extending between the first hole 213 and the cavity 223. The slippery groove 23 is relevant to pair a restraint block 24.

The restraint block 24 is furnished with a slider portion 241 at a bottom thereof to engage and slide along the slippery groove 23. According to this disclosure, the sliding pair of the slider portion 241 and the slippery groove 23 is not limited to those shown in the figure. The restraint block 24 is further furnished with a restraint concavity 242 formed at the end thereof toward the nut 30.

While the restraint block 24 is in a release state as shown in FIG. 3, the restraint block 24 is movable along the slippery groove 23 with respect to the first hole 213 and the cavity 223. While the restraint block 24 is in a constraint state as shown in FIG. 1, opposite ends of the restraint block 24 are individually contacted against the nut 30 and the compression part 40, with the restraint concavity 242 of the restraint block 24 to match a rim of the nut 30.

It shall be explained that, in this embodiment, the design purpose of the restraint block 24 is to form a constraint structure between the first screw 10 and the compression part 40 so as to auxiliary enforce the positioning of the first screw 10 and the compression part 40 by waiving the possibility of obliqueness. If the first screw 10 and the compression part 40 to be mounted firmly and fixedly, then the existence of the restraint block 24 becomes an option.

Referring to FIG. 6A through FIG. 6E, steps for planting the low-profile offset-type spinal fusion device of FIG. 1 into the spine are demonstrated schematically and orderly.

Figure 6A:
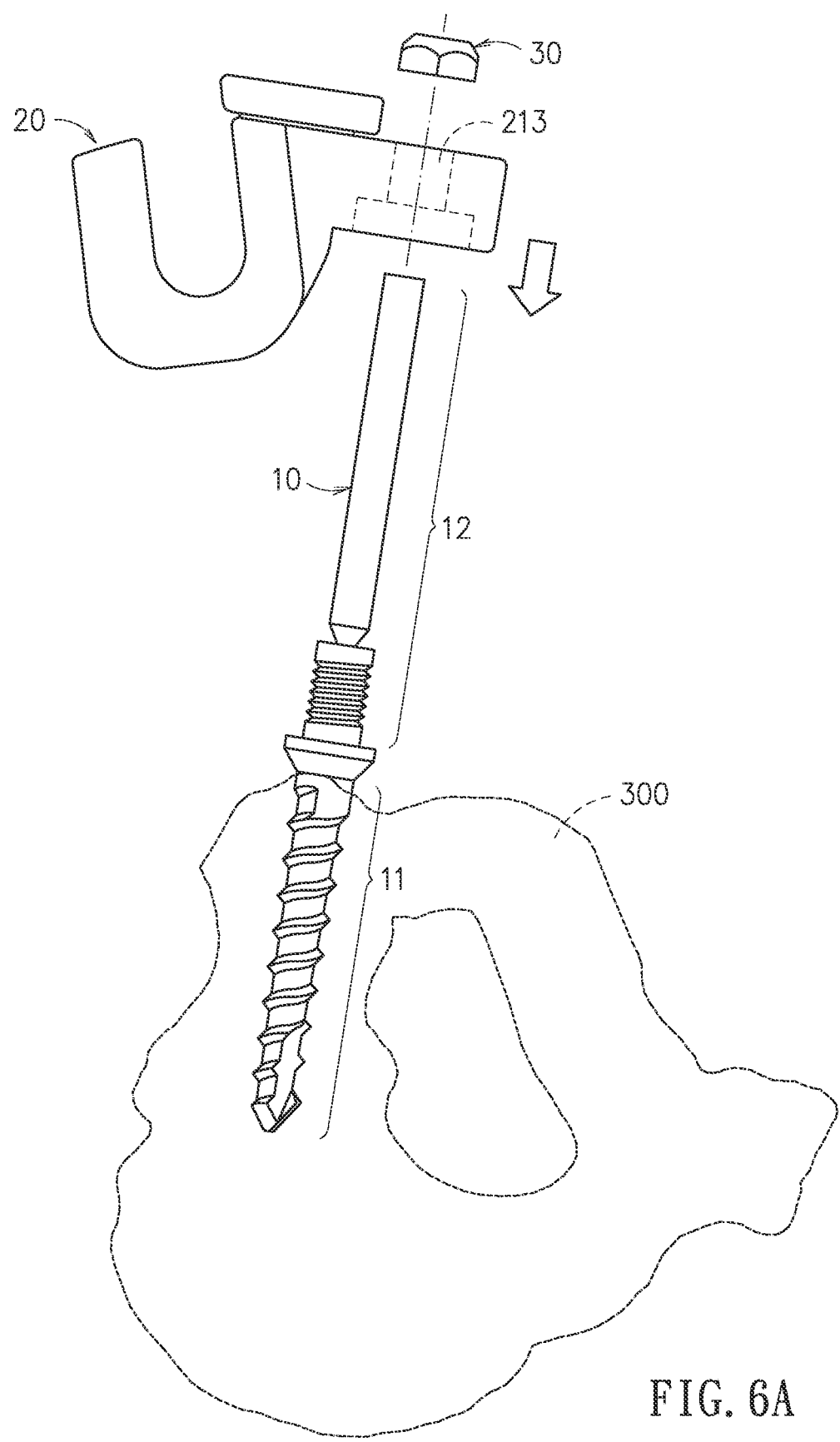
FIG. 6A to FIG. 6E demonstrate schematically and orderly steps for planting the low-profile offset-type spinal fusion device of FIG. 1 into the spine.

As shown in FIG. 6A, firstly. Based on the required angle and position, the first section 11 of the first screw 10 is screwed into the spine 300. Then, the connection base 20 sleeves outside the first screw 10 by having the second section 12 of the first screw 10 to penetrate the first hole 213, and further the nut 30 is applied to sleeve outside the first screw 10.

Figure 6B:
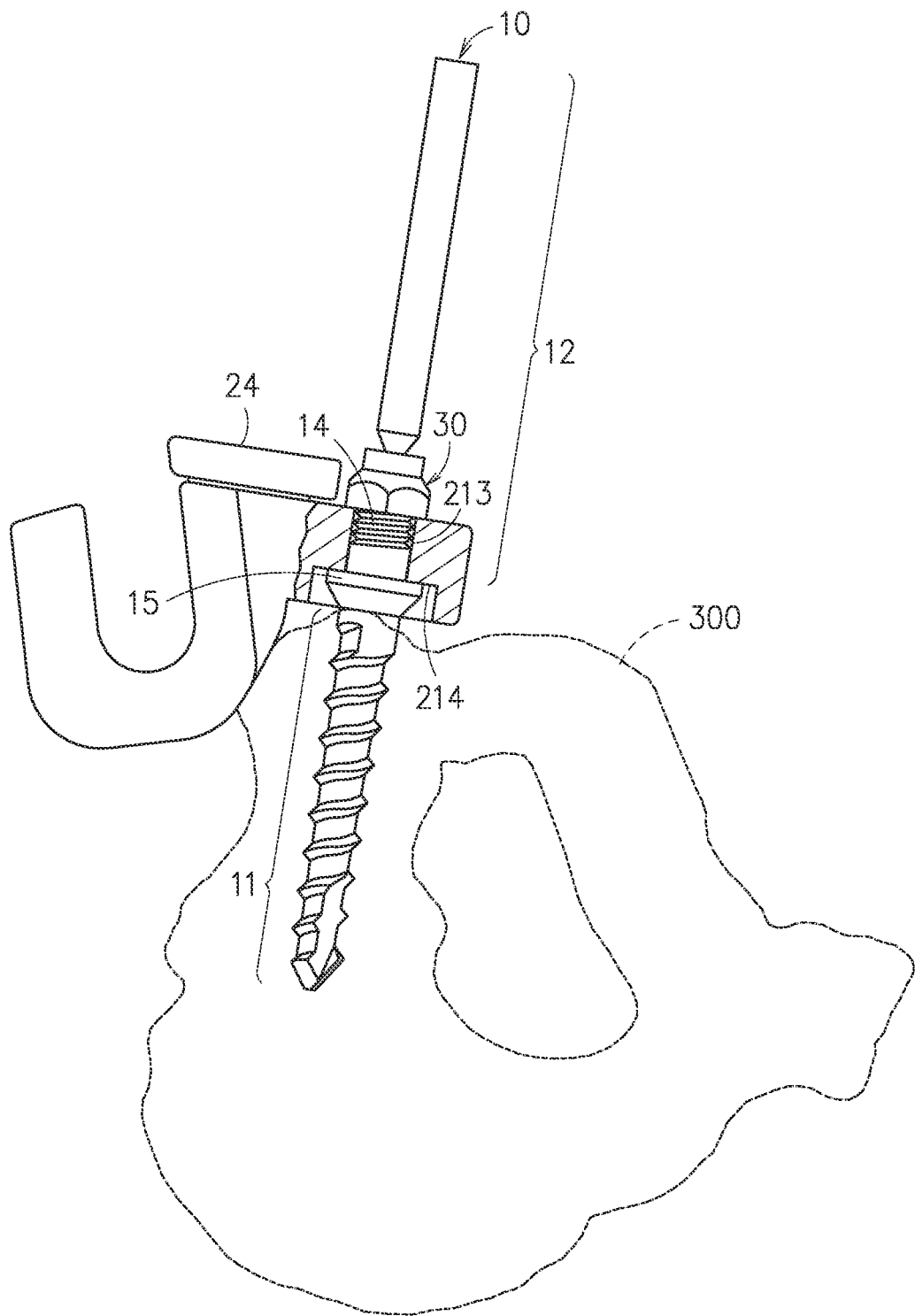

As shown in FIG. 6B, the inner shoulder 214 inside the first hole 213 of the connection base 20 is sent, by sleeving, to contact against the top surface of the flange 15, and then the nut 30 is further applied to engage, by screwing, the second external thread 14 of the first screw 10 so as to have the bottom surface of the nut 30 to contact against the first surface 211 of the penetration part 21. With the nut 30 and the flange 15 to dispose at opposite sides of the first hole 213 in a firm contact manner, then the first screw 10 can be locked up by the first hole 213, and the first section 11 and the second section 12 of the first screw 10 are individually protrusive to opposite sides of the first hole 213. At this time, the restraint block 24 is still in the release state, yet to contact the nut 30.

Figure 6C:
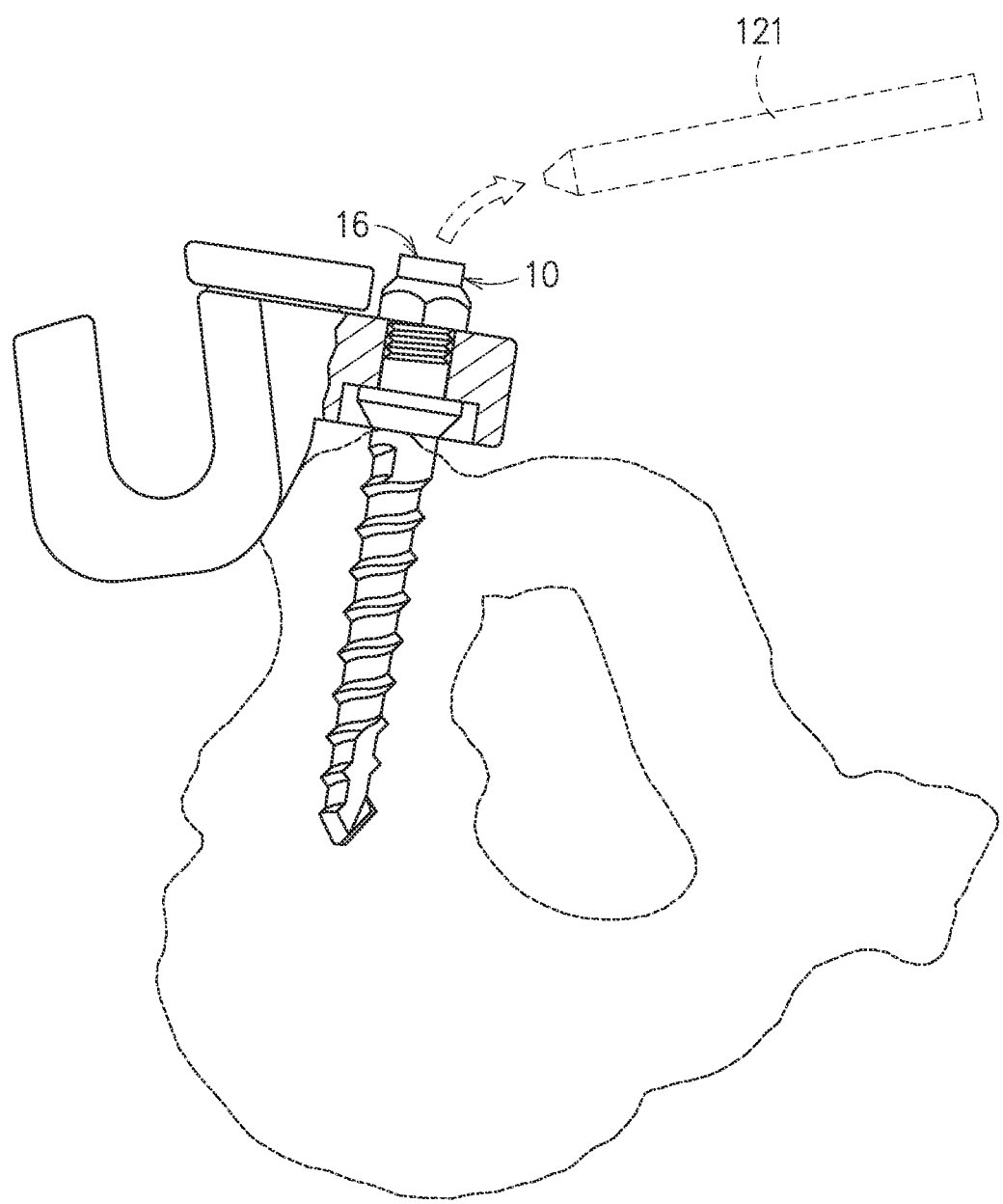

As shown in FIG. 6C, the removable part 121 is bent to break the first screw 10 at the tapered neck area 16, or cut away from the first screw 10 at the tapered neck area 16 by any other appropriate means. With an appropriate arrangement at the tapered neck area 16, the first screw 10 can be broken right at the central breakable interface 163 of FIG. 4, without any burr.

Figure 6D:
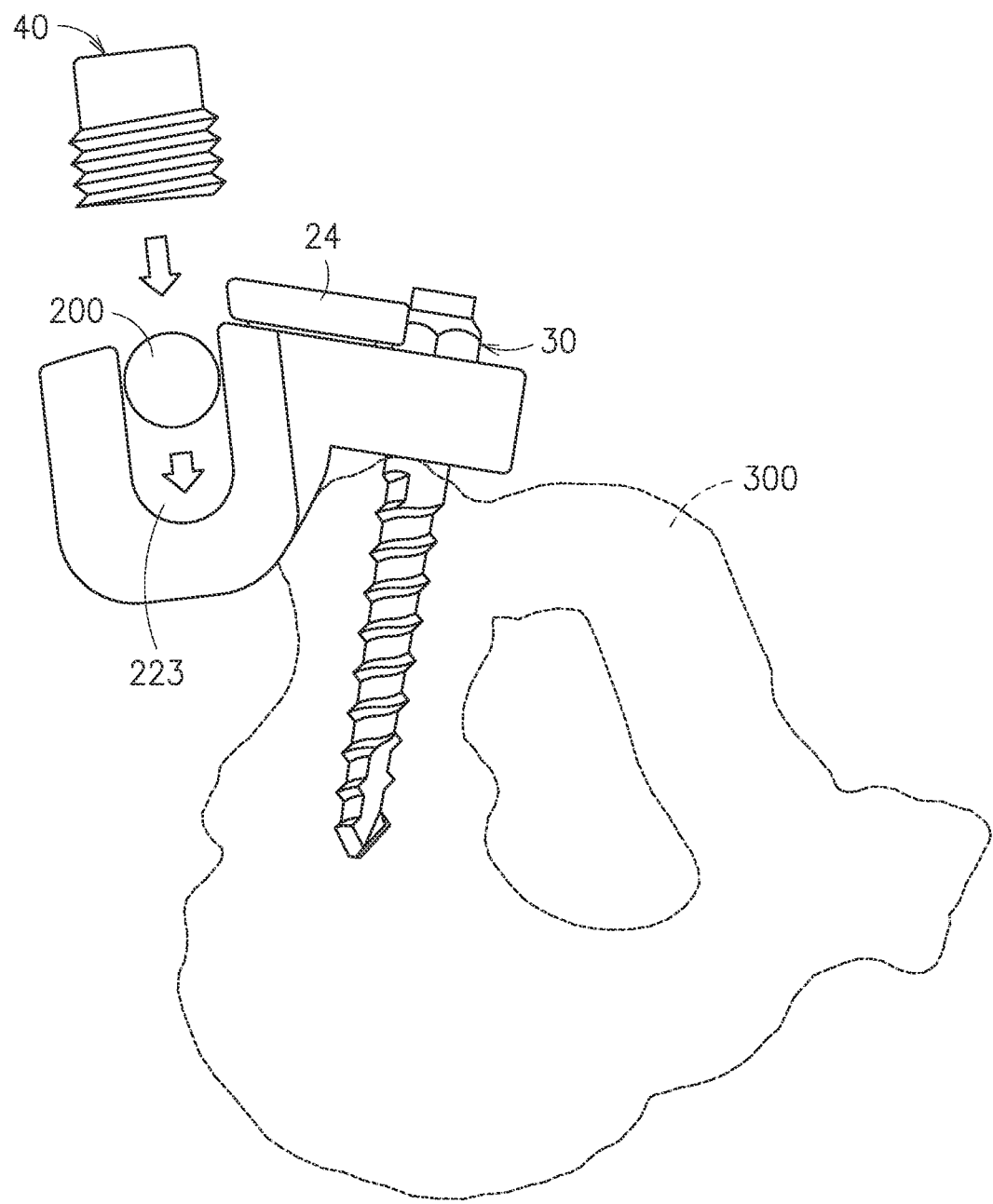

As shown in FIG. 6D, the connecting bar 200 is placed into the cavity 223, then the restraint block 24 is pushed toward the first screw 10, and thus the compression part 40 can be introduced to screw into the cavity 223.

Figure 6E:
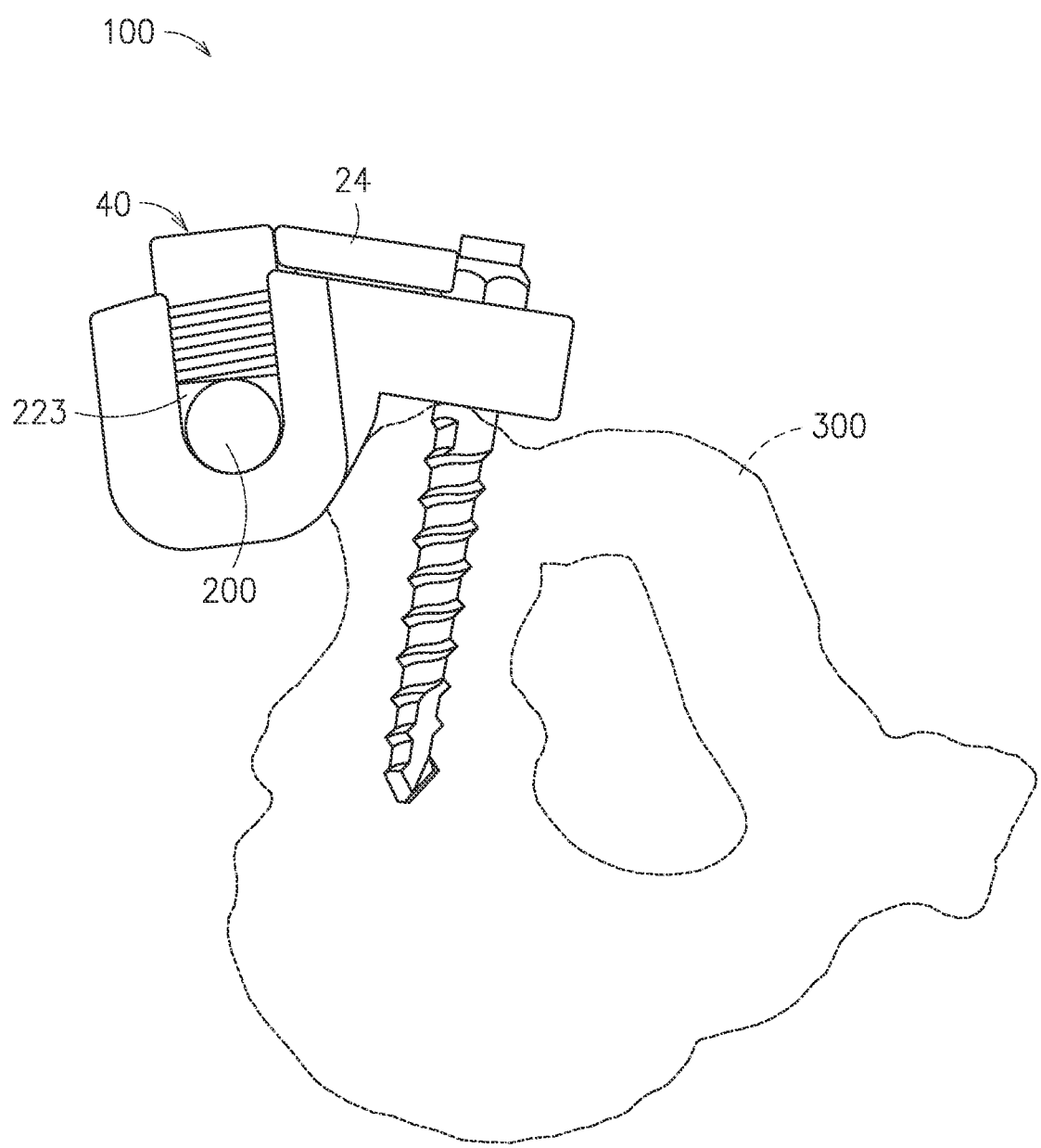

As shown in FIG. 6E, the compression part 40 is screwed down to depress the connecting bar 200 tightly into the cavity 223. In this stage, opposite ends of the restraint block 24 would contact individually against the nut 30 and the compression part 40, respectively. Thereupon, an installation of the low-profile offset-type spinal fusion device 100 at one spine 300 is thus complete. In one embodiment, if a surgery includes a plurality of the low-profile offset-type spinal fusion devices 100 to be installed, then the steps shown from FIG. 6A to FIG. 6C shall be performed repeatedly, then a common connecting bar 200 can be placed into all the cavities 223, and the steps shown from FIG. 6D to FIG. 6E are repeatedly performed at each of the low-profile offset-type spinal fusion devices 100. As such, the installation including the plurality of the low-profile offset-type spinal fusion devices 100 at corresponding spines 300 can be done. In particular, the connecting bar 200 with a specific length is applied to connect the plurality of the low-profile offset-type spinal fusion devices 100 in series.

Regarding the removable part 121 of this disclosure, the design purpose is to provide a handle for the user, so that the first screw 10 can be easily handled to be screwed into the corresponding spine 300. As long as the low-profile offset-type spinal fusion device 100 is successfully installed, then the removable part 121 can be moved away, such that the protrusion of the first screw 10 over the corresponding spine 300 can be reduced.

Figure 7:
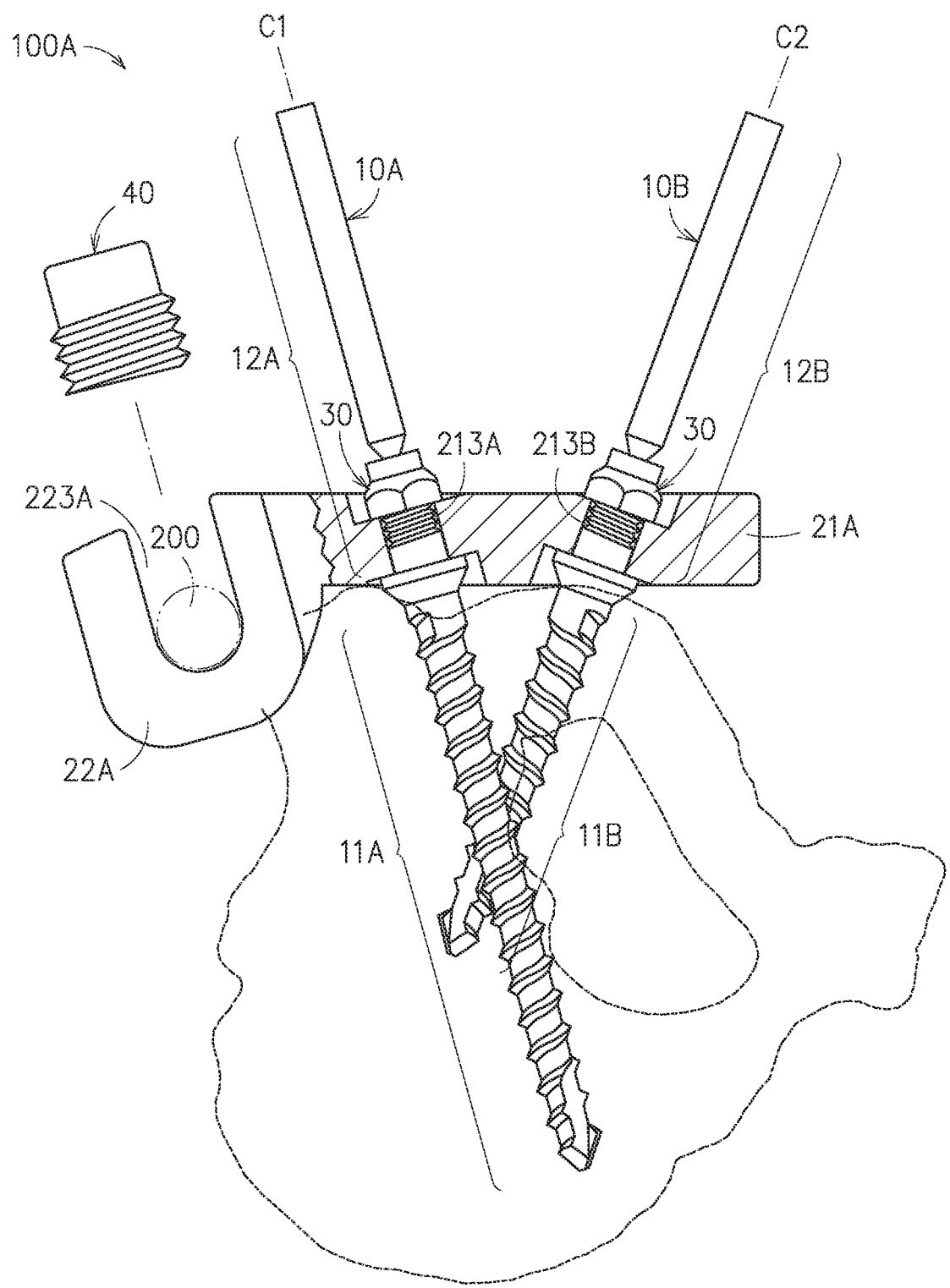
FIG. 7 demonstrates schematically an application of the low-profile offset-type spinal fusion device with two screws in accordance with this disclosure.

FIG. 7 demonstrates schematically an application of the low-profile offset-type spinal fusion device with two screws in accordance with this disclosure. As shown, the low-profile offset-type spinal fusion device 100A includes a first screw 10A, a second screw 10B, a connection base 20A, two nuts 30 and a compression part 40.

The first screw 10A and second screw 10B are structurally resembled to the first screw 10 of FIG. 3. The first screw 10A has a first section 11A and a second section 12A in an axial direction C1. The second screw 10B has a first section 11B and a second section 12B in an axial direction C2. In this embodiment, the first section 11A of the first screw 10A is longer than the first section 11B of the second screw 10B. However, in this disclosure, lengths of the two screws are not limited to the aforesaid embodiment. Practically, lengths of the first screw 10A and the second screw 10B are determined according to actual demands.

The connection base 20A includes a penetration part 21A and a connection part 22A. The connection base 20A of this embodiment is resembled structurally to the connection base 20 of FIG. 3. However, it shall be noted that the penetration part 21A of the connection base 20A is furnished with a first hole 213A and a second hole 213B, to allow the first screw 10A and the second screw 10B to penetrate therethrough, respectively.

In this embodiment, the axial directions C1, C2 of the first hole 213A and the second hole 213B, respectively, are not parallel. After the first screw 10A and the second screw 10B are individually locked up, by screwing, to the first hole 213A and the second hole 213B, respectively, the axial directions C1, C2 of the first screw 10A and the second screw 10B, are crossed spatially. In other words, the axial directions of the first hole 213A and the second hole 213B are spatially crossed. Thus, with such a two-axial design at the low-profile offset-type spinal fusion device 100A according to this disclosure, double locking forcing at the spine 300 can be provided.

By placing the connecting bar 200 into the cavity 223A of the connection part 22A, and then screwing the compression part 40 into the cavity 223A so as to depress the connecting bar 200 tightly in the cavity 223, then an installation of the low-profile offset-type spinal fusion device 100A on the spine 300 is done. If a plurality of the low-profile offset-type spinal fusion devices 100A are included in a surgery, then the steps shown from FIG. 6A to FIG. 6C shall be performed repeatedly, then a common connecting bar 200 can be placed into all the cavities 223A, and the steps shown from FIG. 6D to FIG. 6E are repeatedly performed at each of the low-profile offset-type spinal fusion devices 100A. As such, the installation including the plurality of the low-profile offset-type spinal fusion devices 100A at corresponding spines 300 can be complete. In particular, the connecting bar 200 with a specific length is applied to connect the plurality of the low-profile offset-type spinal fusion devices 100A in series.

In summary, the low-profile offset-type spinal fusion device provided by this disclosure is a less-protrusion spine fixation system for enhancing stability of the spine fixation. In this disclosure, the conventional complicated multi-piece screw head design is improved by lowering and sloping the connection part to approach the corresponding spine for receiving the connecting bar, such that better correction forcing can be provided to the spine. By reducing the length of the screw, the entire profile of the device can be less protrusive with respect to the spine, and thus less friction upon soft tissues, muscles or skins of the patient can be obtained. In addition, by providing the connection base capable of 360° rotation to pair the connecting bar in this disclosure, multi-directional adjustment upon the spines can be provided to comply with the limited anatomical room of the patient. Further, major clinical applications of this disclosure can include, but not limited to, correction and fixation of multiple segments of the lumbar sacral spines (L1~S1), treatments of the congenital vertebral dysplasia, kyphosis, deformity and spinal nerve compression, and the postoperative spine fusion surgery.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A low-profile offset-type spinal fusion device, comprising:
    a first screw, furnished with an external thread and an annular flange;
    a connection base, comprising:
        a penetration part, furnished with a first hole; and
        a connection part, disposed at a side of the penetration part, having a top surface thereof located at the same level as or lower than a top surface of the penetration part, having a cavity for allowing a connecting bar to penetrate therethrough; wherein the connection base utilizes the first hole to sleeve outside the first screw so as to have the first hole to contact against a top portion of the flange, and to have opposite ends of the first screw to protrude out of the first hole;
    a nut, used to engage the first screw, having a bottom surface thereof to contact against the penetration part; wherein, when the first screw is installed by penetrating the first hole, the nut and the flange are located to opposite ends of the first hole;
    a compression part, used to be screwed into the cavity to depress the connecting bar tightly in the cavity; and
    a restraint block, wherein the connection base is furnished with a groove extending longitudinally between the first hole and the cavity, and the groove allows the restraint block to slide along; wherein, when the restraint block is in a release state, the restraint block is able to slide along the groove between the first hole and the cavity; wherein, when the restraint block is in a constraint state, opposite ends of the restraint block are contacted against the nut and the compression part, respectively.

2. The low-profile offset-type spinal fusion device of claim 1, wherein the first screw has a first section and a second section connected linearly with the first section, the first section is furnished with a first external thread, the second section is furnished with a second external thread, the flange is disposed between the first section and the second section, and an outer diameter of the flange is greater than diameters of each of the first section and the second section.

3. The low-profile offset-type spinal fusion device of claim 2, wherein the first hole allows the first screw to penetrate upward via the second section of the first screw, and the first screw is stopped inside the first hole by having the flange to contact against the first hole.

4. The low-profile offset-type spinal fusion device of claim 2, wherein the second section is furnished with a tapered neck area, and the tapered neck area comprises:
    an inverted taper portion, extending axially and shrinking gradually from the second section toward the first section; and
    a concave portion, concaved from the second section toward the first section;
        wherein the concave portion and the inverted taper portion are concentric and connected at a central breakable interface, the central breakable interface has a first diameter, the second section has a second diameter, and the first diameter is smaller than the second diameter.

5. The low-profile offset-type spinal fusion device of claim 4, wherein the first diameter is less than or equal to 1.5 mm.

6. The low-profile offset-type spinal fusion device of claim 2, wherein the nut is to engage, by screwing, the second external thread of the first screw.

7. The low-profile offset-type spinal fusion device of claim 1, wherein the penetration part has oppositely a first surface and a second surface, defined for a top surface and a bottom surface of the penetration part, respectively, and the first hole is extended from the first surface to the second surface; wherein the connection part has oppositely a third surface and a fourth surface, defined for a top surface and a bottom surface of the connection part, respectively, the third surface is disposed at the same level as or lower than the first surface, and the cavity is disposed at the third surface.

8. The low-profile offset-type spinal fusion device of claim 7, wherein the third surface and the first surface are spatially crossed by an angle ranging from 0° to 150°.

9. The low-profile offset-type spinal fusion device of claim 7, wherein the third surface and the first surface are parallel by a distance less than or equal to 40 mm.

10. The low-profile offset-type spinal fusion device of claim 1, wherein an end of the restraint block facing the nut is furnished with a restraint concavity, and the restraint concavity matches a rim of the nut upon when the restraint block is in the constraint state.

11. The low-profile offset-type spinal fusion device of claim 1, further comprising a second screw, wherein the penetration part further has a second hole for allowing the second screw to penetrate therethrough, and axial directions of the first hole and the second hole are crossed spatially.

12. The low-profile offset-type spinal fusion device of claim 1, wherein the cavity is furnished with an internal thread, and the compression part is furnished with an external thread to engage the internal thread of the cavity.

* * * * *